US005877203A

United States Patent [19]
Medford et al.

[11] Patent Number: 5,877,203
[45] Date of Patent: Mar. 2, 1999

[54] TREATMENT FOR ATHEROSCLEROSIS AND OTHER CARDIOVASCULAR AND INFLAMMATORY DISEASES

[75] Inventors: Russell M. Medford; Margaret K. Offermann; R. Wayne Alexander, all of Atlanta, Ga.

[73] Assignee: Emory University, Atlanta, Ga.

[21] Appl. No.: 722,438

[22] Filed: Oct. 17, 1996

Related U.S. Application Data

[60] Continuation of Ser. No. 257,821, Jun. 9, 1994, abandoned, which is a division of Ser. No. 969,934, Oct. 30, 1992, Pat. No. 5,380,747.

[51] Int. Cl.⁶ .......................... A61K 31/40; A61K 31/16; A61K 31/10; A61K 31/55
[52] U.S. Cl. .......................... 514/423; 514/599; 514/712; 514/707; 514/330; 514/212; 514/551
[58] Field of Search ................... 514/423, 599, 514/712, 707, 330, 212, 551

[56] References Cited

U.S. PATENT DOCUMENTS

| | | | |
|---|---|---|---|
| 3,875,170 | 4/1975 | Matsumoto et al. | 260/293.69 |
| 4,056,621 | 11/1977 | Brown et al. | 424/273 R |
| 4,112,104 | 9/1978 | Durant et al. | 424/270 |
| 4,522,811 | 6/1985 | Eppstein et al. | 514/2 |
| 4,670,471 | 6/1987 | Clark | 514/724 |
| 4,868,116 | 9/1989 | Morgan et al. | 435/240.2 |
| 4,870,101 | 9/1989 | Ku et al. | 514/476 |
| 4,900,750 | 2/1990 | Archibald et al. | 514/335 |
| 4,980,286 | 12/1990 | Morgan et al. | 435/172.3 |
| 5,035,878 | 7/1991 | Borch et al. | 424/10 |
| 5,166,133 | 11/1992 | Houston et al. | 514/8 |
| 5,206,264 | 4/1993 | Marangos | 514/483 |
| 5,306,724 | 4/1994 | Goldberg | 514/369 |
| 5,380,747 | 1/1995 | Medford et al. | 514/423 |

FOREIGN PATENT DOCUMENTS

| | | |
|---|---|---|
| A 0 284 879 | 11/1995 | European Pat. Off. |
| 93/01286 | 1/1993 | WIPO |
| 93/01839 | 2/1993 | WIPO |
| 94/09772 | 5/1994 | WIPO |
| 95/30415 | 11/1995 | WIPO |

OTHER PUBLICATIONS

Fruebis, et al., "Evidence for a concerted reaction between lipid hydroperoxides and polypeptides," *Proc. Natl. Acad. Sci. USA*, 89:10588–10592 (1992).

Grigoriev, et al., "A Triple Helix–forming Oligonucleotide–Intercalator Conjugate Acts as a Transcriptional Repressor via Inhibition of NF kB Binding to Interleukin–2 Receptor Alpha–Regulatory Sequence," *J. Biol. Chem.*, 267:3389–3395 (1992).

Holt, et al., "An Oligomer Complementary to c–myc mRNA Inhibits Proliferation of HL–60 Promyelocytic Cells and Induces Differentiation," *Mol. Cell. Biol.*, 8:963–973 (1988).

Kurzawa and Puacz, "Determination of the stability of sodium tetramethylene dithiocarbamate in dilute aqueous solutions by means of the soidum azide–iodine reaction," *Chem. Analy. (Warsaw)*, 23(3):417–20 (1978) (Chemical Abstracts #205007s, 89:475 (1978)).

Lemarie, E., Musset, et al. "Clinical characterization of imuthiol," *Methods Find Exp. Clin. Pharmacol.* 8(1):51–4 (1986).

Marui, et al., "Vascular Cell Adhesion Molecule–1 (VCAM–1) Gene Transcription and Expression are Regulated Through an Antioxidant–Sensitive Mechanism in Human Vascular Endothelial Cells," *J. of Clin. Invest.*, 92(4):1866–1874 (1993).

Menne, T. and K. Kaaber, "Treatment of pompholyx due to nickel allergy with chelating agents," *Contact Dermatitis* 4:(5):289–90 (1978).

Reisinger, et al., "Inhibition of HIV progression by dithiocarb," *Lancet*, 335:679–682 (1990).

Renoux, "Imuthiol.," *Marker Proteins Inflammation*, 3:591–597 (1986), Chemical Abstracts, 105:183515h.

Sarah and Bors, "Radical reactions in vivo–an overview," *Radiat. Environ. Biophys.*, 29(4):249–262 (1990).

Ueyama, "Advancements in plant pharmacology of dithiocarbamates," *Bochu Kagaku*, 32(1):11–19 (1967) (Chemical Abstracts #34892g, 69:3245 (1968)).

Alvarez, D.E.M.J., R. Montoro, et al. (1986), "Determination of cadmium, cooper, and lead in sodium chloride food salts by flame atomic absorption spectroscopy," *J Asoc Off Anal Chem* 68(5): 871–3.

Baselt, R.C., F.W.J. Sunderman, et al. (1977), "Comparisons of antidotal efficacy of sodium diethyldithiocarbamate, D–penicillamine an triethylenetetramine upon acute toxicity of nickel carbonyl in rates," *Res Commun Chem Pathol Pharmacol* 18(4):677–88.

Bjorkhem, I.F., A. Henriksson, et al, (1991), "The antioxidant butylated hydroxytoluene protects against atherosclerosis," *Arterioscler Thromb* 11(1):15–22.

Carew, T.E., D.C. Schwenke, et al., (1987), "Antiatherogenic effect of probucol unrelated to its hypocholesterolemic effect: evidence that antioxidants in vivo can selectively inhibit low density lipoprotein degradation in macrophage–rich fatty streaks and slow the progression of atherosclerosis in the Wantanabe heritable hyperlipidemic rabbit," *Proc Natl Acad Sci U S A* 84(21):7725–9.

Corke, C.F., (1984) "The influence of diethyl–dithiocarbamate ('Imuthiol') on mononuclear cells in vitro," *Int. J. Immunoparmacol* 6(3):245–7.

(List continued on next page.)

*Primary Examiner*—Deborah C. Lambkin
*Attorney, Agent, or Firm*—Sherry M. Knowles; Jacqueline Haley; King & Spalding

[57] ABSTRACT

Dithiocarboxylates, and in particular, dithiocarbamates, block the induced expression of the endothelial cell surface adhesion molecule VCAM-1, and are therefor useful in the treatment of cardiovascular disease, including atherosclerosis, post-angioplasty restenosis, coronary artery diseases, and angina, as well as noncardiovascular inflammatory diseases that are mediated by VCAM-1.

14 Claims, 6 Drawing Sheets

OTHER PUBLICATIONS

Cybulsky, M.I., et al., "Endothelial Expression of a Mononuclear Leukocyte Adhesion Molecule During Atherogensis," *Science* 251 (Feb. 15, 1991) pp. 788–791.

Donner, M., P.K. Husgafvel, et al. (1983), "Mutagenicity of rubber additives and curing fumes. Results from five short–term bioassays," *Scand J Work Envrion Health* 9(2):27–37.

Eltayeb, M.A. and G.R.E. Van (1990), "Iron, copper, zinc and lead in hair from Sudanese populations of different age groups," *Sci Total Environ* 95:157–65.

Evans, R.G., J. Nielsen, et al. (1983), "Enhancement of heat sensitivity and modification of repair of potentially lethal heat damage in plateau–phase cultures of mammalian cells by diethyldithiocarbamate," *Radiat Res* 93(2):319–25.

Fishbein, L. (1976), "Environmental health aspects of fungicides. I. Dithiocarbamates," *J Toxicol Environ Health* 1(5):713–35.

Fishbein, L. (1978), "Overview of potential mutagenic problems posed by some pesticides and their trace impurities," *Environ Health Perspect* 27:125–31.

Gale, G.R., A.B. Smith, et al. (1981), "Diethyldithiocarbamate in treatment of acute cadmium poisoning," *Ann Clin Lab Sci* 11(6):476–83.

Hacker, M.P., W.B. Ershler, et al. (1982). "Effect of disulfiram (tetraethylthiuram disulfide) and diethyldithiocarbamate on the bladder toxicity and antitumor activity of cyclophosphamide in mice," *Cancer Res* 42(11):4490–4.

Hemavathy, K.C. and N. B. Krishnamurthy (1988), "Cytogentic effects of Cuman L, a dithiocarbamate fungicide," *Mutat Res* 208(1):57–60.

Hording, Merete, P.C. Gotzsche, et al. (1990) "Lack of immunomodulating effect of disulfiram on HIV positive patients," *J Immunopharmac* 12(2):145–147.

Iademarco, M.F., et al., "Characterization of the Promoter for Vascular Cell Adhesion Molecule–1 (VCAM–1)," *J. Biol. Chem.*, 267(23), pp. 16323–16329 (1992).

Inoue, K., M. Fukunaga, et al. (1982) "Effect of dislfiram and its reduced metabolite, diethyldithiocarbamate on aldehyde dehydrogenase of human erythrocytes," *Life Sci* 30(5):419–24.

Jones, M.M. and M.G. Cherian (1990), "The search for chelate antagonists for chronic cadmium intoxication," *Toxicology* 62(1):1–25.

Jones, S.G., M.A. Basinger, et al. (1982), "A comparison of diethyldithiocarbamate and EDTA as antidotes for acute cadmium intoxication," *Res Commun Chem Pathol Pharmacol* 38(2):271–8.

Ku, G., N.S. Doherty, et al. (1990), "Ex vivo lipopolysaccharide–induced interleukin–1 secretion from murine peritoneal macrophages inhibited by probucol, a hypocholesterolemic agent with *antioxidant* proprieties," *Faseb J* 4(6): 1645–53.

Lang, J.M., C. Trepo, et al. (1988), "Randomised, double–blind, placebo–controlled trial of ditocarb sodium ('Imuthiol') in human immunodeficiency virus infection," *The Lancet* Sep. 24, 1988:702–706.

Lin, P.S., L. Kwock, et al. (1980) "Copper chelator enhancement of bleomycin cytotoxicity," *Cancer* 46(11):2360–4.

Marui, N., et al., "Vascular Cell Adhesion Molecule–1 (VCAM–1) Gene Transcription and Expression are Regulated Through an Antioxidant–Sensitive Mechanism in Human Vascular Endothelial Cells," *J. Clin. Invest.*, 92 Oct. 1993, pp. 1866–1874.

*The Merck Index* (1989) Merck & Co., Inc., Rahway, New Jersey, 11th Ed., p. 533.

Miller, D.B. (1982), "Neurotoxicity of the pesticidal carbamates," *Neurobehav Toxicol Teratol* 4(6):779–87.

Moerlein, S.M., A. Daugherty, et al. (1991), "Utility of Tc–99m–and in–111–labelled low–density lipoprotein as radiopharmaceuticals for metabolic imaging," *J Nuclear Medicine* 32:(1) 925–926.

Pages, A., J.S. Casas, et al. (1985), "Dithiocarbamates in heavy metal poisoning: complexes of N,N–di(2–hidroxyethyl)dithiocarbamate with Zn(II), Cd(II), Hg(II), CH3Hg(II), and C6H5Hg(II)." *J Inorg Biochem* 25(1):35–42.

Paller, M.S., J.R. Hoidal, et al. (1984), "Oxygen fee Radicals in Ischemic acute renal failure in the rat," *J Clin Invest* 74:1156–1164.

Parthasarathy, S., S.G. Young, et al. (1986). "Probucol inhibits oxidative modification of low density lipoprotein." *J Clin Invest* 77(2):641–4.

Perchellet, E.M., E.A. Maatta, et al. (1987). "Effects of Diverse Intracellular Thoil Delivery Agents on Glutathione Peroxidase Activity, the Ratio of Reduced/Oxidized Glutathione, and Ornithine Decarboxylase Induction in Isolated Mouse Epidermal Cells Treated with 12–O–Tetradecanoylphorbal–13–Acetate." *J Cell Physiol* 131:64–73.

Perkins, N.D., et al., "Distinct Combinations of NF–kB Subunits Determine the Specificity of Transcriptional Activation," *Proc. Natl. Acad. Sci.*, 89 pp. 1523–1533, Mar. 1992.

Pober, J.S. and R.S. Cotran (1991), "What can be learned from the expression of endothelial adhesion molecules in tissues? [editorial]." *Lab. Invest.* 64:301–305.

Pompidou, A., M.C. Delsaux, et al. (1985). "Isoprinosine and Imthiol, two potentially active compounds in patients with AIDS–related complex symptoms." *Cancer Res:*..

Quinto, I. and M.E. De (1983) "Evaluation of Propineb, a dithiocarbamate pesticide, in the mouse–sperm morphology assay," *Mutat Res* 124(3–4):235–40.

Rannug, A. and U. Rannug (1984). Enzyme inhibition as a possible mechanism of the mutagenicity of dithiocarbamic acid derivatives in Salmonella typhimurium.: *Chem Biol Interact* 49(3):329–40.

Renoux, G. (1986). "Characterization of immunotherapeutic agents: the example of imuthoil." *Methods Find Exp Clin Pharmacol* 8(1):45–50.

Renoux, G. (1988). "The cortex regulates the immune system and the activities of a T–cell specific immunopotentiator." *Int J. Neurosci* 39(1–2):177–87.

Renoux, M.J.P. Giroud, et al. (1986). "Early changes in immune parameters induced by an acute nonantigenic inflammation in mouse: influence of imuthiol." *Int J Immunopharmacol* 8(1):107–17.

Rice, G.E., J.M. Munro, et al. (1991). "Vascular and non-vascular expression of INCAM–110. A target for mononuclear leukocyte adhesion in normal and inflamed human tissues." *Am J Pathol* 128(2):385–93.

Robinson, K.A., et al., "Effects of a Thiol Antioxidant on Leucocyte Adherence to Aortic Endothelium During Atherogenesis: Quantitative Sem Assessment," *Proc. 51st Annual Meeting of the Microscopy Society of America* (1993).

Schreck, R., B. Meier, et al. (1992). "Dithiocarbamates as Potent Inhibitors of Nuclear Factor kB Activation in Intact Cells." *J. Exp. Med.* 175:1181–1194.

Schreck, R., P. Rieber, et al. (1991). "Reactive oxygen intermediates as apparently widely used messengers in the activation of the NF–kappa B transcription factor and HIC–1." *Embo J* 10(8):2247–58.

Steinberg, D., S. Parthasarathy, et al. (1989). "Beyond cholesterol: modifications of low–density lipoprotein that increase its atherogenicity." *N. Engl. J. Med.* 320:915–924.

Steinberg, D. and W. Participants (1992). "Antioxidants in the Prevention of Human Atherosclerosis." *Circulation* 85:2338–2344.

Sunderman, F.W. (1978), "Clinical response to *therapeutic* agents in poisoning from mercury vapor." *Ann Clin Lab Sci* 8(4):259–69.

Sunderman, F.W. (1979). "Efficacy of sodium diethyldithiocarbamate (dithiocarb) in acute nickel carbonyl poisoning." *Ann Clin Lab Sci* 9(1):1–10.

Tandon, S.K., N.S. Hashmi, et al. (1990). "The lead–chelating effects of substituted dithiocarbamates." *Biomed Environ Sci* 3(3):299–305.

Topping, R.J. and M.M. Jones (1988). "Optimal dithiocarbamate structure for immunomodulator action." *Med Hypothese* 27(1):55–7.

Tripathy, N.K., B. Majhi, et al. (1989). "Genotoxicity of ziram established through wing, eye and female germ–line mosaic assays and the sex–linked recessive lethal test in Drosophila melanogaster." *Mutat Res* 224(2):161–9.

Walker, Jr., E.M., et al., "Antipseudomonal Effects of Selected Dithiocarbamates Alone and In Combination with Gentamicin or Aztreonam," *Res. Comm. Chem. Path. Pharm.* 63(1) Jan. 1989, pp. 101–107.

Warner, B.B., M.S. Burhans, et al. (1991). "Tumor necrosis factor–alpha increases Mn–SOD expression: protection against oxidant injury." *Am J Physiol* .

Martindale, "Disulfiram and Citrated Calcium Carbimide." *The Extra Pharmacopoeia*, 28th Edition, p. 579 (1985).

Menne and Kaaber, "Treatment of pompholyx due to nickel allergy with chelating agents," *Contact Dermatitis*, 4(5):289–290 (1978).

Neish, et al., "Functional Analysis of the Human Vascular Cell Adhesion Molecule 1 Promoter," *J. Exp. Med.*, 176:1583–1593 (1992).

Thorn and Ludwig, *The Dithiocarbamates and Related Compounds*, pp. 1–298 (Publisher, Elsevier Publishing Company, Amsterdam, New York, 1962).

SODIUM PYRROLIDINE-*N*-CARBODITHIOATE

SODIUM *N*-METHYL-*N*-CARBOXYMETHYL-*N*-CARBODITHIOATE (OR SODIUM SARCOSINEDITHIOCARBAMATE)

TRISODIUM *N*,*N*-di(CARBOXYMETHYL)-*N*-CARBODITHIOATE (OR IMINODIACETIC ACID DITHIOCARBAMATE, TRISODIUM)

SODIUM *N*-METHYL-D-GLUCAMINE-*N*-CARBODITHIOATE

SODIUM *N*-(4-METHOXYBENZYL)-D-GLUCAMINE-*N*-CARBODITHIOATE

SODIUM *N*,*N*-DIETHYL-*N*-CARBODITHIOATE (OR SODIUM DIETHYLDITHIOCARBAMATE)

SODIUM *N*,*N*-DIISOPROPYL-*N*-CARBODITHIOATE (OR SODIUM DIISOPROPYLDITHIOCARBAMATE)

TREATMENT FOR ATHEROSCLEROSIS AND OTHER CARDIOVASCULAR AND INFLAMMATORY DISEASES

This application is a continuation of U.S. Ser. No. 08/257,821 filed on Jun. 9, 1994, abandoned, which is a divisional of U.S. Ser. No. 07/969,934 filed on Oct. 30, 1992 (now U.S. Pat. No. 5,380,747).

BACKGROUND OF THE INVENTION

This application is in the area of methods and compositions for the treatment of atherosclerosis and other cardiovascular and inflammatory diseases.

Adhesion of leukocytes to the endothelium represents a fundamental, early event in a wide variety of inflammatory conditions, including atherosclerosis, auto immune disorders and bacterial and viral infections. This process is mediated in part by the induced expression of endothelial cell surface adhesion molecules, such as ICAM-1 (intracellular adhesion molecule-1), VCAM-1 (vascular adhesion molecule-1) and ELAM-1 (endothelial leukocyte adhesion molecule-1). These adhesion molecules bind to immune cells, which initiate and propagate the inflammatory response. One of the adhesion molecules, VCAM-1, plays an especially important role in binding monocytes. Multiple signals induce the expression of the cell surface adhesion molecules.

Atherosclerosis is a chronic inflammatory disease of the arterial intima characterized by the focal accumulation of leukocytes, smooth muscle cells, lipids and extracellular matrix. A central feature, and one of the earliest detectable events, in the pathogenesis of atherosclerotic plaque is the adherence of mononuclear leukocytes to discrete segments of the arterial endothelium through the VCAM-1 proteins on the surface of the vascular endothelial cells. After attachment to the endothelial cells, the mononuclear leukocytes are transformed into lipid-laden macrophages, or "foam cells". Atherosclerosis begins as a highly focal lesion within the vascular wall usually in areas where the normal, laminar flow of blood is disturbed such as at vessel flow dividers. These "low shear stress" areas are characterized by an abnormal local accumulation of oxidatively-modified low density lipoprotein (ox-LDL).

It has been suggested that early events in the pathogenesis of atherosclerosis are mediated by low density lipoprotein that has been converted by reactive oxygen species into ox-LDL. Steinberg, et al., "Beyond cholesterol: Modifications of low-density lipoprotein that increase its atherogenicity." *N. Engl. J. Med.* 320: 915–924 (1989); Parthasarathy, et al., "Probucol inhibits oxidative modification of low density lipoprotein." *J Clin Invest* 77(2): 641–4 (1986). It is not clear by what mechanism LDL is oxidized either intracellularly or extracellularly.

Current therapies for cardiovascular disease, and in particular, atherosclerosis do not treat the cause of the disease, but instead treat the symptoms of the disease or lower risk factors associated with the disease. Pharmaceutical agents prescribed for these conditions include lipid lowering agents such as probucol and nicotinic acid; aspirin (which prevents platelets from sticking); antithrombotic agents such as coumadin; calcium channel blockers such as varapamil, diltiazem, and nifedipine; angiotensin converting enzyme (ACE) inhibitors such as captopril and enalopril, and β-blockers such as propanalol, terbutalol, and labetalol. Since the therapeutic agents are not selective, they affect many different organs, and have significant side effects.

There are currently no drugs that are directed at inhibiting the binding of monocytes to cell surface adhesion molecules such as VCAM-1.

Given that cardiovascular disease is currently the leading cause of death in the United States, and ninety percent of cardiovascular disease is presently diagnosed as atherosclerosis, there is a strong need to identify new methods and pharmaceutical agents for their treatment.

Dithiocarbamates are transition metal chelators clinically used for heavy metal intoxication. Baselt, R. C., F. W. J. Sunderman, et al. (1977), "Comparisons of antidotal efficacy of sodium diethyldithiocarbamate, D-penicillamine and triethylenetetramine upon acute toxicity of nickel carbonyl in rats." *Res Commun Chem Pathol Pharmacol* 18(4): 677–88; Menne, T. and K. Kaaber (1978), "Treatment of pompholyx due to nickel allergy with chelating agents." *Contact Dermatitis* 4(5): 289–90; Sunderman, F. W. (1978), "Clinical response to therapeutic agents in poisoning from mercury vapor" *Ann Clin Lab Sci* 8(4): 259–69; Sunderman, F. W. (1979), "Efficacy of sodium diethyldithiocarbamate (dithiocarb) in acute nickel carbonyl poisoning." *Ann Clin Lab Sci* 9(1): 1–10; Gale, G. R., A. B. Smith, et al. (1981), "Diethyldithiocarbamate in treatment of acute cadmium poisoning." *Ann Clin Lab Sci* 11(6): 476–83; Jones, M. M. and M. G. Cherian (1990), "The search for chelate antagonists for chronic cadmium intoxication." *Toxicology* 62(1): 1–25; Jones, S. G., M. A. Basinger, et al. (1982), "A comparison of diethyldithiocarbamate and EDTA as antidotes for acute cadmium intoxication." *Res Commun Chem Pathol Pharmacol* 38(2): 271–8; Pages, A., J. S. Casas, et al. (1985), "Dithiocarbamates in heavy metal poisoning: complexes of N,N-di(1hydroxyethyl)dithiocarbamate with Zn(II), Cd(II), Hg(II), CH3Hg(II), and C6H5Hg(II).: *J. Inorg Biochem* 25(1): 35–42; Tandon, S. K., N. S. Hashmi, et al. (1990), "The lead-chelating effects of substituted dithiocarbamates." *Biomed Environ Sci* 3(3): 299–305.

Dithiocarbamates have also been used adjunctively in cis-platinum chemotherapy to prevent renal toxicity. Hacker, M. P., W. B. Ershler, et al. (1982). "Effect of disulfiram (tetraethylthiuram disulfide) and diethyldithiocarbamate on the bladder toxicity and antitumor activity of cyclophosphamide in mice." *Cancer Res* 42(11): 4490–4. Bodenner, 1986 #733 Chelation of transition metals would have the effect of blocking hydroxyl radical production intracellular via the Haber-Weiss-Fenton reaction). Saran, M. and Bors, W. (1990). "Radical reactions in vivo—an overview." *Radiat. Environ. Biophys.* 29(4):249–62.

A dithiocarbamate currently used in the treatment of alcohol abuse is disulfiram, a dimer of diethyldithiocarbamate. Disulfuram inhibits hepatic aldehyde dehydrogenase. Inoue, K., and Fukunaga, et al., (1982). "Effect of disulfiram and its reduced metabolite, diethyldithiocarbamate on aldehyde dehydrogenase of human erythrocytes." *Life Sci* 30(5): 419–24.

It has been reported that dithocarbamates inhibit HIV virus replication, and also enhance the maturation of specific T cell subpopulations. This has led to clinical trials of diethyldithiocarbamate in AIDs patient populations. Reisinger, E., et al., (1990). "Inhibition of HIV progression by dithiocarb." *Lancet* 335: 679.

It is therefore an object of the present invention to provide a method for the treatment of atherosclerosis and other cardiovascular and inflammatory diseases.

It is another object of the present invention to provide pharmaceutical compositions for the treatment of atherosclerosis and other cardiovascular and inflammatory diseases.

It is still another object of the present invention to provide methods and compositions to block the ability of cells to express gene products known to be responsible for the adherence of leukocytes to those cells, and activation of the cells.

SUMMARY OF THE INVENTION

It has been discovered that dithiocarboxylates, and in particular, dithiocarbamates, block the induced expression of the endothelial cell surface adhesion molecule VCAM-1, and thus are useful in the treatment of atherosclerosis, post-angioplasty restenosis, coronary artery diseases, angina, and other cardiovascular diseases, as well as non-cardiovascular inflammatory diseases that are mediated by VCAM-1.

Importantly, certain dithiocarbamates, such as sodium pyrrolidine N-dithiocarbamate (PDTC), do not significantly block the induced expression of other endothelial cell surface adhesion molecules, such as ICAM-1 or ELAM-1, and therefore, do not adversely affect inflammatory responses that VCAM-1 does not mediate. It has also been discovered that PDTC exhibits preferential toxicity to proliferating or abnormally dividing vascular smooth muscle cells. Another dithiocarbamate, sodium N-methyl-N-carboxymethyl-N-carbodithioate, also inhibits the expression of VCAM-1, without significant effect on ICAM-1, but does not exhibit preferential toxicity to abnormally dividing vascular smooth muscle cells. The ability of the other active dithiocarbamates to selectively inhibit the expression of VCAM-1 (without inhibiting the expression of ELAM-1 or ICAM-1), and to exhibit preferential toxicity to abnormally dividing smooth muscle cells, is evaluated according to methods disclosed herein.

Dithiocarbamates that are useful in the treatment of atherosclerosis and other cardiovascular and inflammatory diseases include, but are not limited to, those of the formulas:

wherein $R^1$ is H or a pharmaceutically acceptable cation, including but not limited to sodium, potassium, or $NR^4R^5R^6R^7$, wherein $R^4$, $R^5$, $R^6$, and $R^7$ are independently hydrogen, $C_{1-6}$ linear, branched, or cyclic alkyl, hydroxy($C_{1-6}$)alkyl (wherein one or more hydroxyl groups are located on any of the carbon atoms), or aryl, and $R^2$ and $R^3$ are independently $C_{1-10}$ linear, branched or cyclic alkyl; —(CHOH)$_n$(CH$_2$)$_n$OH, wherein n is 0, 1, 2, 3, 4, 5, or 6; —(CH$_2$)$_n$CO$_2$R$^1$, —(CH$_2$)$_n$CO$_2$R$^4$; hydroxy($C_{1-6}$)alkyl—, or $R^2$ and $R^3$ together constitute a bridge such as —(CH$_2$)$_m$—, wherein m is 3–6, and wherein $R^4$ is alkyl, aryl, alkaryl, or aralkyl, including acetyl, propionyl, and butyryl.

The active dithiocarboxylates, and in particular dithiocarbamates, disclosed herein can be used in the treatment of acute and chronic inflammatory diseases mediated by VCAM-1, including but not limited to rheumatoid and osteoarthritis, asthma, dermatitis, and may be of benefit in the treatment of multiple sclerosis.

The compounds are useful in both the primary and adjunctive medical treatment of cardiovascular disease. The compounds can be used as adjunctive therapy in combination with agents administered to reduce the risk of disease by lowering LDL and serum cholesterol. The method represents a significant advance in treating cardiovascular disease, in that it goes beyond the current therapies designed simply to inhibit the progression of the disease, and when used appropriately, provides the possibility to medically "cure" atherosclerosis by preventing new lesions from developing and causing established lesions to regress. The compounds can be administered to treat small vessel disease that is not treatable by surgery or angioplasty, or other vessel disease in which surgery is not an option. The compounds can also be used to stabilize patients prior to revascularization therapy.

The active compound or a mixture of the compounds are administered in any appropriate manner, including but not limited to orally and intravenously. General range of dosage will be from 0.5 to 500 mg/kg body weight with a dose schedule ranging from once every other day to twice a day. The length of dosing will range from a single dose given only once to twice daily to dosages given over the course of two to six months.

The compounds can also be administered directly to the vascular wall using perfusion balloon catheters following or in lieu of coronary or other arterial angioplasty. As an example, 2–5 mL of a physiologically acceptable solution that contains approximately 1 to 500 μM of the compound or mixture of compounds is administered at 1–5 atmospheres pressure. Thereafter, over the course of the next six months during the period of maximum risk of restenosis, the active compounds are administered through other appropriate routes and dose schedules.

Relatively short term treatments with the active compounds are used to cause the "shrinkage" of coronary artery disease lesions that cannot be treated either by angioplasty or surgery. A nonlimiting example of short term treatment is two to six months of a dosage ranging from 0.5 to 500 mg/kg body weight given at periods ranging from once every other day to three times daily.

Longer term treatments can be employed to prevent the development of advanced lesions in high-risk patients. A long term treatment can extend for years with dosages ranging from 0.5 to 500 mg/kg body weight administered at intervals ranging from once every other day to three times daily.

The active compounds can also be administered in the period immediately prior to and following coronary angioplasty as a means to reduce or eliminate the abnormal proliferative and inflammatory response that currently leads to clinically significant restenosis.

The active compounds can be administered in conjunction with other medications used in the treatment of cardiovascular disease, including lipid lowering agents such as probucol and nicotinic acid; platelet aggregation inhibitors such as aspirin; antithrombotic agents such as coumadin; calcium channel blockers such as varapamil, diltiazem, and nifedipine; angiotensin converting enzyme (ACE) inhibitors such as captopril and enalopril, and β-blockers such as propanalol, terbutalol, and labetalol. The compounds can also be administered in combination with nonsteroidal anti-inflammatories such as ibuprofen, indomethacin, fenoprofen, mefenamic acid, flufenamic acid, sulindac, or with corticosteriods.

BRIEF DESCRIPTION OF THE FIGURES

FIG. 4 indicates that multiple regulatory signals induce VCAM-1 but not ICAM-1 through a common, dithiocarbamate-sensitive pathway in human vascular endothelial cells.

DETAILED DESCRIPTION OF THE INVENTION

The term alkyl, as used herein, unless otherwise specified, refers to a saturated straight, branched, or cyclic hydrocarbon of $C_1$ to $C_{10}$, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl.

The term alkenyl, as referred to herein, and unless otherwise specified, refers to a straight, branched, or cyclic hydrocarbon of $C_2$ to $C_{10}$ with at least one double bond.

The term alkynyl, as referred to herein, and unless otherwise specified, refers to a $C_2$ to $C_{10}$ straight or branched hydrocarbon with at least one triple bond.

The term aralkyl refers to an aryl group with at least one alkyl substituent.

The term alkaryl refers to an alkyl group that has at least one aryl substituent.

The term halo (alkyl, alkenyl, or alkynyl) refers to an alkyl, alkenyl, or alkynyl group in which at least one of the hydrogens in the group has been replaced with a halogen atom.

The term aryl, as used herein, and unless otherwise specified, refers to phenyl or substituted phenyl, wherein the phenyl ring has one or more of the following substituents: hydroxy, $CO_2H$, or its pharmaceutically acceptable salt, $CO_2$(alkyl), alkoxy, alkyl or glucamine.

The term alkoxy, as used herein, and unless otherwise specified, refers to a moiety of the structure —O-alkyl.

The term halo, as used herein, includes fluoro, chloro, bromo, and iodo.

The term hydroxyalkyl, as used herein, refers to a $C_1$ to $C_6$ alkyl group in which at least one of the hydrogens attached to any of the carbon atoms is replaced with a hydroxy group.

The term thiol antioxidant refers to a sulfur containing compound that retards oxidation.

The term pharmaceutically acceptable derivative refers to a derivative of the active compound that upon administration to the recipient, is capable of providing directly or indirectly, the parent compound, or that exhibits activity itself.

I. Active Compounds

It has been discovered that dithiocarboxylates are useful in the treatment of atherosclerosis and other cardiovascular and inflammatory diseases. Dithiocarboxylates, including dithiocarbamates, can be used to block the ability of cells, including endothelial cells, to express VCAM-1, which is a gene product known to be responsible for the adherence of leukocytes to cells. The fact that dithiocarboxylates, including dithiocarbamates, inhibit VCAM-1 gene expression strongly supports the importance of oxidation as an initiating signal in altered vascular-inflammatory cell interactions. The specific molecular mechanisms by which the dithiocarboxylates function in inhibiting VCAM-1 gene expression is not known.

At least one of the compounds, sodium pyrrolidine dithiocarbamate (PDTC), inhibits VCAM-1 gene expression at a concentration of less than 1.0 micromolar. This compound also exhibits preferential toxicity to proliferating or abnormally dividing vascular smooth muscle cells. It has been discovered that sodium pyrrolidine dithiocarbamate does not significantly block ELAM-1 or ICAM-1 expression, and therefore treatment with this compound does not adversely affect aspects of the inflammatory response mediated by ELAM-1 or ICAM-1. Thus, a generalized immunosuppression is avoided. This may avoid systemic complications from generalized inhibition of adhesion molecules in the many other cell types known to express them.

Dithiocarboxylates are compounds of the structure A-SC(S)-B, which are members of the general class of compounds known as thiol antioxidants, and are alternatively referred to as carbodithiols or carbodithiolates. It appears that the SC(S) moiety is essential for therapeutic activity, and that A and B can be any group that does not adversely affect the efficacy or toxicity of the compound. A and B can be selected by one of ordinary skill in the art to impart desired characteristics to the compound, including size, charge, toxicity, and degree of stability (including stability in an acidic environment such as the stomach, or basic environment such as the intestinal tract). The selection of A and B will also have an important effect on the tissue-distribution and pharmacokinetics of the compound. In general, for treatment of cardiovascular disease, it is desirable that the compound accumulate, or localize, in the arterial intimal layer containing the vascular endothelial cells. The compounds are preferably eliminated by renal excretion.

As nonlimiting examples, A and B can be independently alkyl, alkenyl, alkynyl, alkaryl, aralkyl, haloalkyl, haloalkenyl, haloalkynyl, aryl, alkaryl, hydrogen, $C_{1-6}$ alkoxy-$C_{1-10}$ alkyl, $C_{1-6}$ alkylthio-$C_{1-10}$ alkyl, $C_{1-10}$ substituted alkyl (wherein the substituent is independently hydroxy, carbonyl, or carboxylic acid, located on any of $C_{1-10}$) $NR^2R^3$, —$(CHOH)_nCH_2OH$, wherein n is 0, 1, 2, 3, 4, 5, or 6, —$(CH_2)_nCO_2R^1$, including acetyl, propionyl, and butyryl, hydroxy($C_{1-6}$)alkyl (wherein one or more hydroxyl groups are located on any of the carbon atoms), and A can be a pharmaceutically acceptable cation, including but not limited to sodium, potassium, or $NR^4R^5R^6R^7$. In an alternative embodiment, a dimer such as B-C(S)S-SC(S)-B can be administered.

Dithiocarboxylates should be chosen for use in treating atherosclerosis and other cardiovascular and inflammatory diseases that have the proper lipophilicity to locate at the affected site. The compound should not compartmentalize in low turnover regions such as fat deposits. In a preferred embodiment for treatment of cardiovascular disease, the pharmacokinetics of the compound should not be dramatically affected by congestive heart failure or renal insufficiency.

The dithiocarboxylate must be physiologically acceptable. In general, compounds with a therapeutic index of at least 2, and preferably at least 5 or 10, are acceptable. The therapeutic index is defined as the $EC_{50}/IC_{50}$, wherein $EC_{50}$ is the concentration of compound that inhibits the expression of VCAM-1 by 50% and $IC_{50}$ is the concentration of compound that is toxic to 50% of the target cells. Cellular toxicity can be measured by direct cell counts, trypan blue exclusion, or various metabolic activity studies such as 3H-thymidine incorporation, as known to those skilled in the art. The therapeutic index of PDTC in tissue culture is over 100 as measured by cell toxicity divided by ability to inhibit VCAM-1 expression activated by TNFa, in HUVE (human umbilical vein) cells. Initial studies on the rapidly dividing cell type HT-18 human glioma demonstrate no toxicity at concentrations 100-fold greater than the therapeutic concentration. Disulfiram, an orally administered form of diethyldithiocarbamate, used in the treatment of alcohol abuse, generally elicits no major clinical toxicities when administered appropriately.

There are a few dithiocarbamates that are known to be genotoxic. These compounds do not fall within the scope of the present invention, which is limited to the administration of physiologically acceptable materials. An example of a genotoxic dithiocarbamate is the fungicide zinc dimethyldithiocarbamate. Further, the anticholinesterase properties of certain dithiocarbamates can lead to neurotoxic effects. Miller, D. (1982). Neurotoxicity of the pesticidal carbamates. *Neurobehav. Toxicol. Teratol.* 4(6): 779–87.

The term dithiocarboxylate as used herein specifically includes, but is not limited to, dithiocarbamates of the formulas:

$R^1SC(S)NR^2R^3$ and $R^2R^3N(S)CS\text{-}SC(S)NR^2R^3$ wherein $R^1$ is H or a pharmaceutically acceptable cation, including but not limited to sodium, potassium, or $NR^4R^5R^6R^7$, wherein $R^4$, $R^5$, $R^6$, and $R^7$ are independently hydrogen, $C_{1-6}$ linear, branched, or cyclic alkyl, hydroxy($C_{1-6}$)alkyl (wherein one or more hydroxyl groups are located on any of the carbon atoms), or aryl, and $R^2$ and $R^3$ are independently $C_{1-10}$ linear, branched or cyclic alkyl; —$(CHOH)_n(CH_2)_nOH$, wherein n is 0, 1, 2, 3, 4, 5, or 6; —$(CH_2)_nCO_2R^1$, —$(CH_2)_nCO_2R^4$; hydroxy($C_{1-6}$)alkyl—, or $R^2$ and $R^3$ together constitute a bridge such as —$(CH_2)_m$—, wherein m is 3–6, and wherein $R^4$ is alkyl, aryl, alkaryl, or aralkyl, including acetyl, propionyl, and butyryl.

Figure 8:
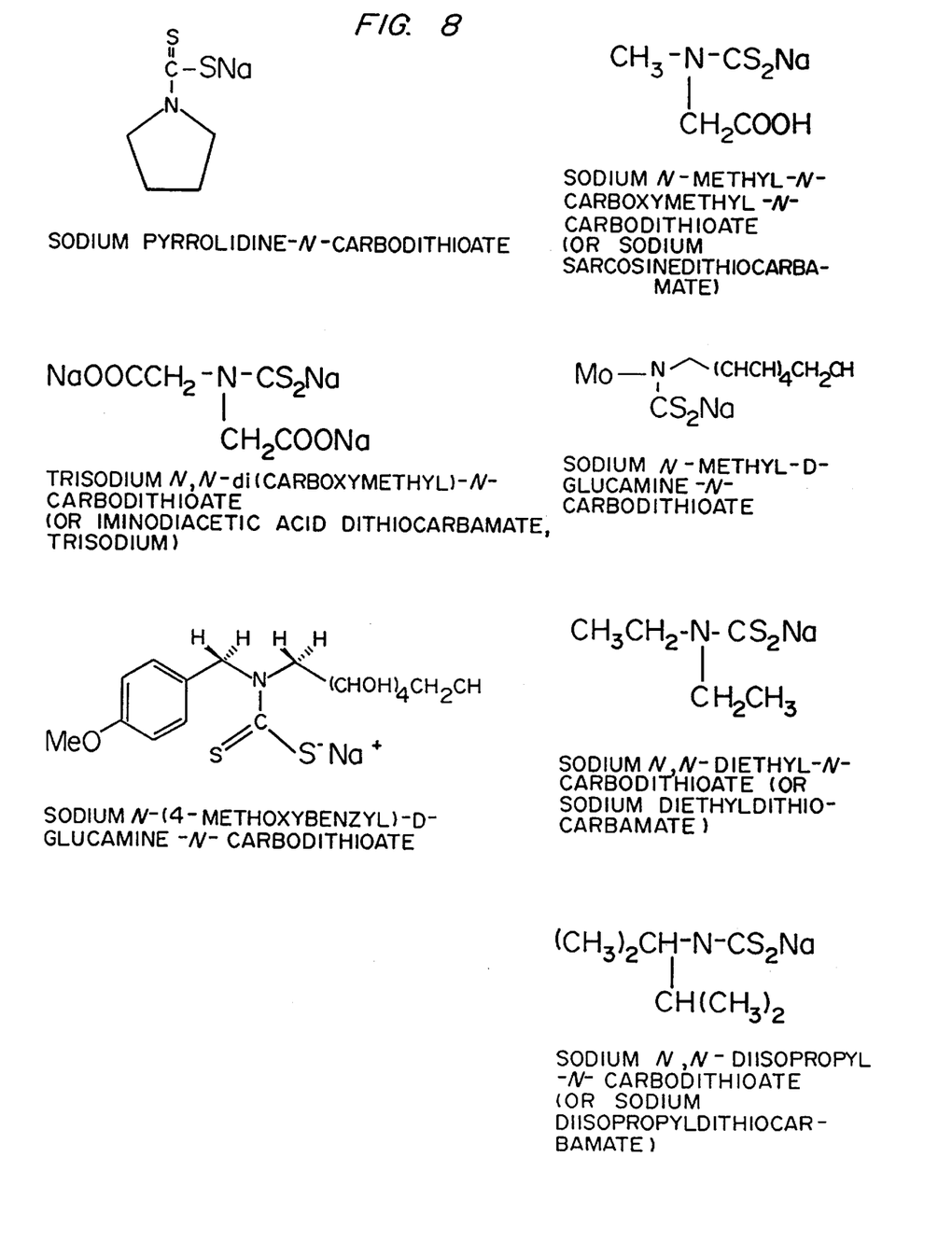
FIG. 8 is an illustration of the chemical structures of the following active dithiocarbamates: sodium pyrrolidine-N-carbodithioate, sodium N-methyl-N-carboxymethyl-N-carbodithioate, trisodium N,N-di(carboxymethyl)-N-carbodithioate, sodium N-methyl-D-glucamine-N-carbodithioate, sodium N,N-diethyl-N-carbodithioate (sodium diethyldithiocarbamate), and sodium N,N-diisopropyl-N-carbodithioate.

Specific examples of useful dithiocarbamates, illustrated in FIG. 8, include sodium pyrrolidine-N-carbodithioate, sodium N-methyl-N-carboxymethyl-N-carbodithioate, trisodium N,N-di(carboxymethyl)-N-carbodithioate, sodium N-methyl-D-glucamine-N-carbodithioate, sodium N,N-diethyl-N-carbodithioate (sodium diethyldithiocarbamate), and sodium N,N-diisopropyl-N-carbodithioate.

The active dithiocarboxylates and in particular, dithiocarbamates are either commercially available or can be prepared using known methods.

At the molecular level, PDTC has been shown to inhibit the activation of the transcriptional regulatory factor Nf-kB in response to certain cytokine and non-cytokine stimuli (Schreck, Rieber et al. 1991; Schreck, Meier et al. 1992). However, by gel mobility shift assay of HUVEC nuclear extracts with various kB-like enhancer motifs, it has been discovered that endothelial cells activate VCAM-1 gene expression through an apparently novel transcriptional regulatory factor that is not Nf-kB. This suggests that PDTC may regulate endothelial cell gene expression through its effect on a new transcriptional regulatory protein. It has also been demonstrated that VCAM-1 expression is induced by multiple factors in cultured Kaposi's sarcoma cells, which may be important in its pathogenesis. PDTC blocks VCAM-1 expression in Kaposi's sarcoma cells that have been activated by TNF, IL-1, and poly(I:C).

It has also been discovered that smooth muscles cells produce a soluble form of VCAM-1 which may be secreted by the cells, and which may act as a natural antihistamine.

II. Biological Activity

The ability of dithiocarboxylates to inhibit the expression of VCAM-1 can be measured in a variety of ways, including by the methods set out in detail below in Examples 1 to 7. For convenience, Examples 1–3 and 6–7 describe the evaluation of the biological activity of sodium pyrrolidine-N-carbodithioate (also referred to as PDTC). These examples are not intended to limit the scope of the invention, which specifically includes the use of any of the above-described compounds to treat atherosclerosis, and other types of inflammation and cardiovascular disease mediated by VCAM-1. Any of the compounds described above can be easily substituted for PDTC and evaluated in similar fashion.

Examples 4 and 5 provide comparative data on the ability of a number of dithiocarbamates to inhibit the gene expression of VCAM-1. The examples below establish that the claimed dithiocarbamates specifically block the ability of VCAM-1 to be expressed by vascular endothelial cells in response to many signals known to be active in atherosclerosis and the inflammatory response.

Experimental Procedures

Cell Cultures

HUVE cells were isolated from human umbilical veins that were cannulated, perfused with Hanks solution to remove blood, and then incubated with 1% collagenase for 15 minutes at 37° C. After removal of collagenase, cells were cultured in M199 medium supplemented with 20% fetal bovine serum (HyClone), 16 µg/ml heparin (ESI Pharmaceuticals, Cherry Hill, N.J.), 50 µg/ml endothelial cell growth supplement (Collaborative Research Incorporated, Bedford Mass.), 25 mM Hepes Buffer, 2 mM L-glutamin, 100 µg/ml penicillin and 100 µg/ml streptomycin and grown at 37° C. on tissue culture plates coated 0.1% gelatin. Cells were passaged at confluency by splitting 1:4. Cells were used within the first 8 passages.

Incubation with Cytokines and Other Reagents

Confluent HUVE cells were washed with phosphate buffered saline and then received fresh media. The indicated concentrations of PDTC were added as pretreatment 30 minutes before adding cytokines. Cytokines and other inducers were directly added to medium for the times and at the concentrations indicated in each experiment. Human recombinant IL-lb was the generous gift of Upjohn Company (Kalamazoo, Mich.). TNFa was obtained from Bohringer Engelheim. Bacterial lipopolysaccharide (LPS), polyinosinic acid: polycitidilic acid (Poly I:C), and pyrrolidine dithiocarbamate (PDTC) were obtained from Sigma Chemical (St. Louis, Mo.). All other reagents were of reagent grade.

RNA Isolation:

Total cellular RNA was isolated by a single extraction using an acid guanidium thiocyanate-phenol-chloroform mixture. Cells were rinsed with phosphate buffered saline and then lysed with 2 ml of guanidium isothiocyanate. The solution was acidified with 0.2 ml of sodium acetate (pH 4.0) and then extracted with 2 ml phenol and 0.4 ml chloroform:isoamyl alcohol (24:1). The RNA underwent two ethanol precipitations prior to being used for Northern blot analysis.

Northern Blot Analysis:

Total cellular RNA (20 µg) was size fractionated using 1% agarose formaldehyde gels in the presence of 1 µg/ml ethidium bromide. The RNA was transferred to a nitrocellulose filter and covalently linked by ultraviolet irradiation using a Stratlinker UV crosslinker (Stratagene, La Jolla, Calif.). Hybridizations were performed at 42° C. for 18 hours in 5X SSC (1X=150 mM NaCl, 15 mM Na citrate), 1% sodium dodecyl sulfate, 5X Denhardt solution, 50% formamide, 10% dextran sulfate and 100 µg/ml of sheared denatured salmon sperm DNA. Approximately 1–2 X $10^6$ cpm/ml of labeled probe (specific activity>$10^8$ cpm/µg DNA) were used per hybridization. Following hybridization, filters were washed with a final stringency of 0.2 X SSC at 55° C. The nitrocellulose was stripped using boiled water prior to rehybridization with other probes. Autoradiography was performed with an intensifying screen at −70° C.

$^{32}$Probes:

$^{32}$P labeled DNA probes were made using the random primer oligonucleotide method. The ICAM-1 probe was an Eco R1 fragment of human cDNA. The ELAM-1 probe was a 1.85 kb Hind III fragment of human cDNA. The VCAM-1 probe was a Hind III-Xho I fragment of the human cDNA consisting of nucleotide 132 to 1814.

Enzyme Linked Immunosorbent Assay (ELISA):

HUVE cells were plated on 96-well tissue culture plates 48 to 72 hours before the assay. Primary antibodies in M199 with 5% FBS were added to each well and incubated one hour at 37° C. The cells were then washed and incubated for one hour with peroxidase conjugated goat anti-mouse IgG (Bio Rad) diluted 1/500 in M199 with 5% FBS. The wells were then washed and binding of antibody was detected by the addition of 100 µl of 10 mg/ml 3,3,5,5'-tetramethylbenzidine (Sigma) with 0.003% $H_2O_2$. The reaction was stopped by the addition of 25 µl of 8N sulfuric acid. Plates were read on an ELISA reader (Bio Rad) at OD 450 nm after blanking on rows stained only with second step antibody. Data represent the means of triplicate.

Antibodies:

Monoclonal antibody (MAb) 4B9 recognizing vascular cell adhesion molecule-1 (VCAM-1) was the generous gift of Dr. John Harlan (University of Washington). MAb E9A1F1 recognizing endothelial cell adhesion molecule (ELAM-1) was the generous gift of Dr. Swerlick (Emory University). Hybridomas producing mAb 84H10 recognizing intercellular adhesion molecule 1 (ICAM-1) are routinely grown in our laboratory and antibody was used as tissue culture supernatant.

EXAMPLE 1

PDTC Blocks IL-lb Mediated Induction of HUVEC VCAM-1, but not ICAM-1 or ELAM-1, mRNA Accumulation To determine whether the oxidative state of the endothelial cell can alter the basal or induced expression of cell adhesion molecule genes, cultured human vascular endothelial cells were exposed to the inducing cytokine, IL-lb (10

Figure 1A:
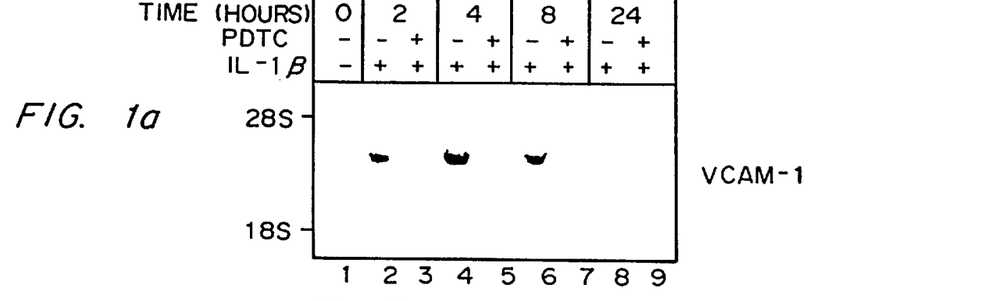
FIGS. 1A, 1B and 1C are illustrations of an autoradiogram of mRNA, obtained as described below, hybridized to either $^{32}$p labeled human VCAM-1 specific cDNA (FIG. 1A), E-selectin (ELAM-1) specific cDNA (FIG. 1B), or ICAM-1 specific cDNA (FIG. 1C). Following pre-treatment for 30 minutes with 50 μM of sodium pyrrolidine dithiocarbamate (PDTC), HUVE (human umbilical vein) cells were exposed to IL-lb (10 U/ml) in the continuous presence of 50 μM PDTC. Parallel controls were performed identically except in the absence of PDTC. At the indicated times, total RNA was isolated and 20 μg of material size-fractionated by denaturing 1.0% agarose-formaldehyde gel electrophoresis, transferred to nitrocellulose, hybridized as described above, and visualized by autoradiography. Lane 1-0 hour; Lanes 2,4,6,8–OL-1 alone for 2, 4, 8 and 24 hours, respectively; Lanes 3,5,7,9–IL-1 with PDTC for 2,4,8 and 24 hours, respectively.
Figure 1B:
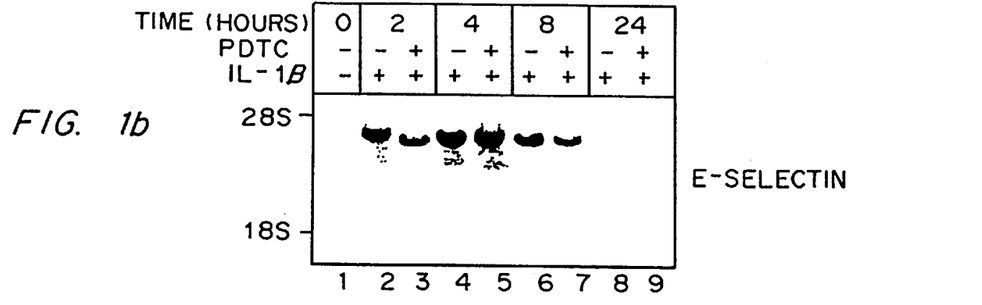
Figure 1C:
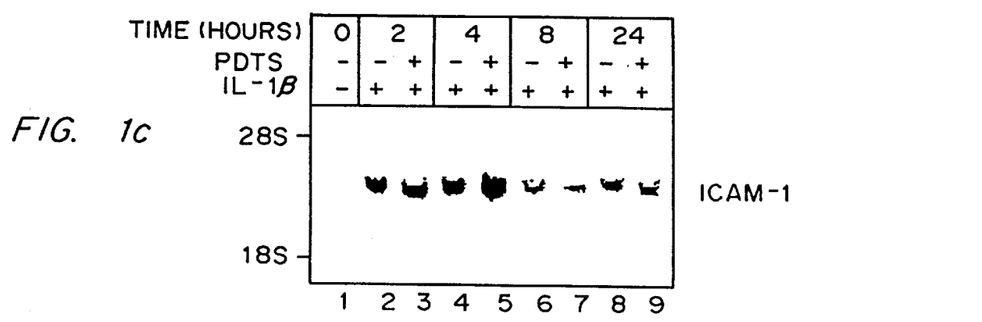

U/ml) in the presence or absence of the thiolated metal chelating antioxidant, pyrrolidine dithiocarbamate (PDTC, 50 µM) for up to 24 hours. As shown in FIG. 1, IL-lb alone (lanes 2, 4, 6, 8) induces the expected rapid and transient induction of VCAM-1 (Panel A), E-selectin (ELAM-1, Panel B) and ICAM-1 (Panel C) mRNA accumulation, all of which peak at four hours. However, in the presence of PDTC, IL-lb induction of VCAM-1 mRNA accumulation is dramatically inhibited by over 90% (panel A, lanes 3, 5, 7, 9). In contrast, although IL-lb mediated induction of ELAM-1 is slightly inhibited at 2 and 24 hours (compare lane 2 and 3, 8 and 9, panel B), PDTC does not inhibit the induction at 4 and 8 hours (lane 5 and 7, panel B). IL-lb mediated induction of ICAM-1 mRNA accumulation is not affected (panel B, lanes 3, 5, 7, 9). Indeed, a mild augmentation of IL-lb induction of ICAM-1 mRNA accumulation (~30%) is observed (compare lanes 4 and 5, panel B). Equivalent amounts of nitrocellulose transferred RNA per lane was confirmed by ethidium bromide staining and visualization.

Figure 2A:
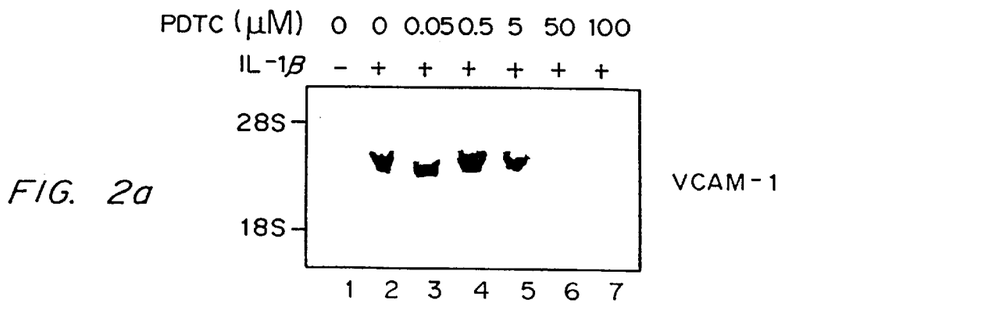
FIGS. 2A, 2B, and 2C are illustrations of an autoradiogram of mRNA, obtained as described below, hybridized to either $^{32}p$ labeled human VCAM-1 specific (FIG. 2A), E-selectin (ELAM-1) specific cDNA (FIG. 2B), or ICAM-1 specific cDNA (FIG. 2C). HUVE cells were pretreated with the indicated concentrations of PDTC, and then exposed to IL-lb in the presence of PDTC for four hours and assayed for VCAM-1 mRNA accumulation by Northern filter hybridization analysis. Lane 1–control, lane 2–IL-1 (10 u/ml), lane 3–IL-lb+PDTC (0.05 μM), lane 4–IL-1 LB+PDTC (0.5 μM), lane 5–IL-lb+PDTC (5.0 μM), lane 6–IL=lb+PDTC (50.0 μM), lane 7–IL-lb+PDTC (100 μM).
Figure 2B:
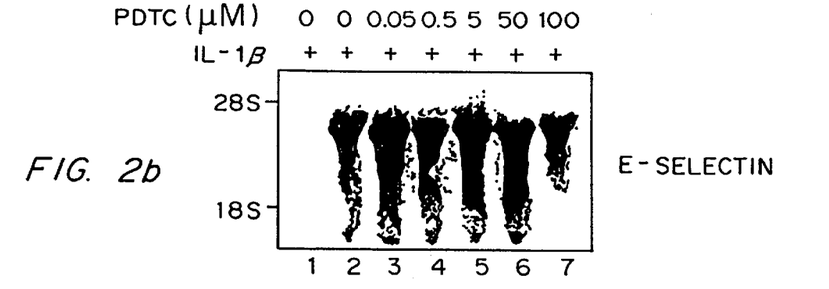
Figure 2C:
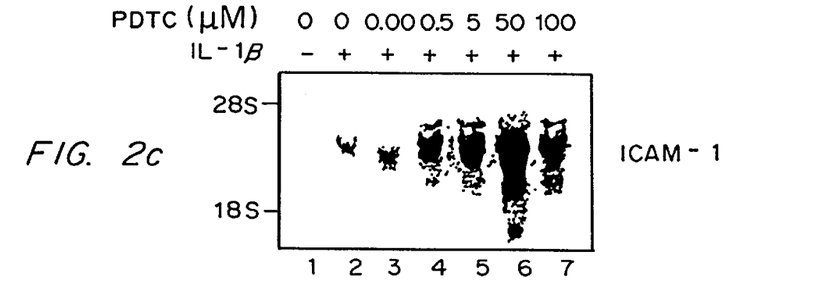

A dose-response analysis was performed to determine whether PDTC inhibits the induction of VCAM-1 gene expression by IL-lb in a dose dependent manner. As shown in FIG. 2, PDTC inhibits IL-lb mediated induction of VCAM-1 gene expression with a steep dose-response curve (FIG. 2, panel A) with a calculated $EC_{50}$ of approximately 10 µM, while PDTC does not inhibit IL-lb mediated induction of ELAM-1 expression with these concentrations (FIG. 2, panel B). The IL-lb mediated induction of ICAM-1 mRNA accumulation is enhanced by PDTC with the concentration higher than 0.5 µM (FIG. 2, compare lane 2 and lane 4–7, panel C).

These data demonstrate that IL-lb utilizes a dithiocarboxylate, and in particular, a dithiocarbamate sensitive step as part of its signaling mechanism in the induction of VCAM-1 gene expression. The data also appear to indicate that this dithiocarbamate sensitive step does not play a significant role in the IL-lb mediated induction of ELAM-1 or ICAM-1 gene expression.

EXAMPLE 2

PDTC Blocks Induction of HUVEC VCAM-1 mRNA Accumulation by Multiple Stimuli

Figure 3A:
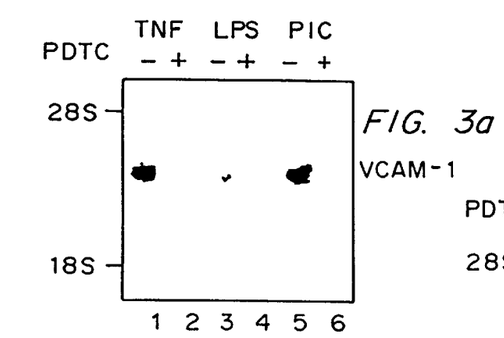
FIGS. 3A, 3B, and 3C are illustrations of an autoradiogram of mRNA, obtained as described below, hybridized to either $^{32}p$ labeled human VCAM-1 specific cDNA (FIG. 3A), E-selectin (ELAM-1) specific cDNA (FIG. 3B), or ICAM-1 specific cDNA (FIG. 3C). HUVE cells were pretreated as described in FIGS. 1A–1C with 50 μM PDTC, exposed for four hours to the agents indicated below, and assayed for VCAM-1 (FIG. 3A) and ICAM-1 (FIG. 3B) mRNA accumulation. Lane 1–TNFa (100 U/ml), lane 2–TNFa+PDTC, lane 3–lipopolysaccharide (LPS) (100 ng/ml), lane 4–LPS+PDTC, lane 5–poly(I:C) (100 mg/ml), lane 6–poly(I:C)+PDTC.
Figure 3B:
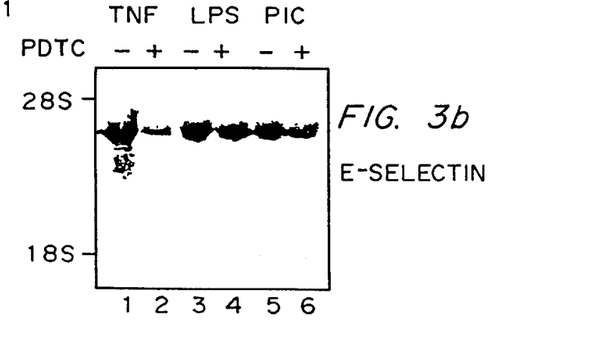
Figure 3C:
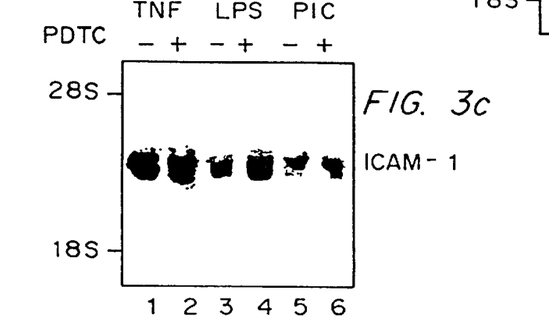

To determine whether other well-described activators of VCAM-1 gene expression also utilize a PDTC sensitive step, three distinct classes of activators were tested: another classic receptor mediated inducing agent (tumor necrosis factor, TNFa), a non-receptor mediated inducer (lipopolysaccharide, LPS) and a recently described novel inducer (double stranded RNA, poly(I:C)). In all three cases, PDTC dramatically inhibited the induction of VCAM-1 mRNA accumulation in HUVECs after four hours (FIG. 3, Panel A). Although the TNFa mediated ELAM-1 gene expression is suppressed to some extent (FIG. 3 lane 1 and 2, panel B), LPS and poly(I:C) mediated ELAM-1 mRNA accumulation was unaffected (FIG. 3 lane 3–6, panel B). The induction of ICAM-1 mRNA accumulation was unaffected (FIG. 3, Panel C). This data indicates that structurally distinct inducing agents, acting through distinct pathways, share a common regulatory step specific for the induction of VCAM-1 gene expression.

EXAMPLE 3

PDTC Blocks HUVE Cell Surface Expression of VCAM-1 Induced by Multiple Stimuli

Figure 4:
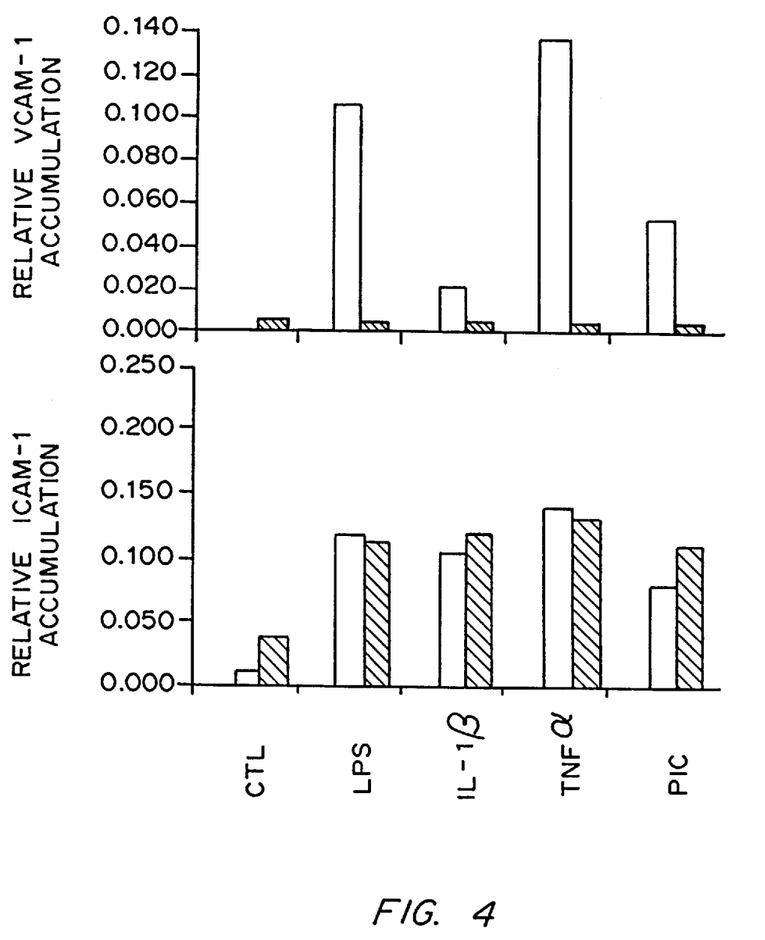
FIG. 4 is a graph of relative cell surface expression of VCAM-1 and ICAM-1 in the presence (dark bars) or absence (white bars) of PDTC and in the presence of multiple types of inducing stimuli. Confluent HUVECs were pretreated or not pretreated (CTL only) for 30 minutes with 50 μM PDTC, and then exposed for the indicated times to the indicated agents in the presence or absence (CTL only) of PDTC. Cell surface expression was determined by primary binding with VCAM-1 specific (4B9) and ICAM-1 specific (84H10) mouse monoclonal antibodies followed by secondary binding with a horse-radish peroxidase tagged goat anti-mouse (IgG). Quantitation was performed by determination of calorimetric conversion at 450 nm of TMB.

To determine whether, like its mRNA, the induction of endothelial cell surface protein expression of VCAM-1 could also be inhibited by PDTC, monoclonal antibodies were used in an ELISA assay to quantitate the induction of cell surface VCAM-1 and ICAM-1 in cultured HUVE cells. As shown in FIG. 4, multiple classes of activating agents, in the absence of PDTC (–PDTC), induce the rapid and transient accumulation of VCAM-1 (top left panel) at the cell surface peaking at six hours. In the presence of PDTC (+PDTC, top right panel), the induction of cell surface expression of VCAM-1 by all agents tested is dramatically inhibited (80–90%). In contrast, the induced expression of cell surface ICAM-1 is unaffected under identical conditions (bottom left and right panels).

These data demonstrate that, like its mRNA accumulation, cell surface VCAM-1 expression are selectively inhibited by dithiocarbamates and that multiple classes of activating agents utilize a similar, dithiocarbamate sensitive mechanism to induce VCAM-1 gene expression.

EXAMPLE 4

Comparative Effectiveness of Antioxidants in Blocking TNFa Induction of VCAM-1

Figure 5:
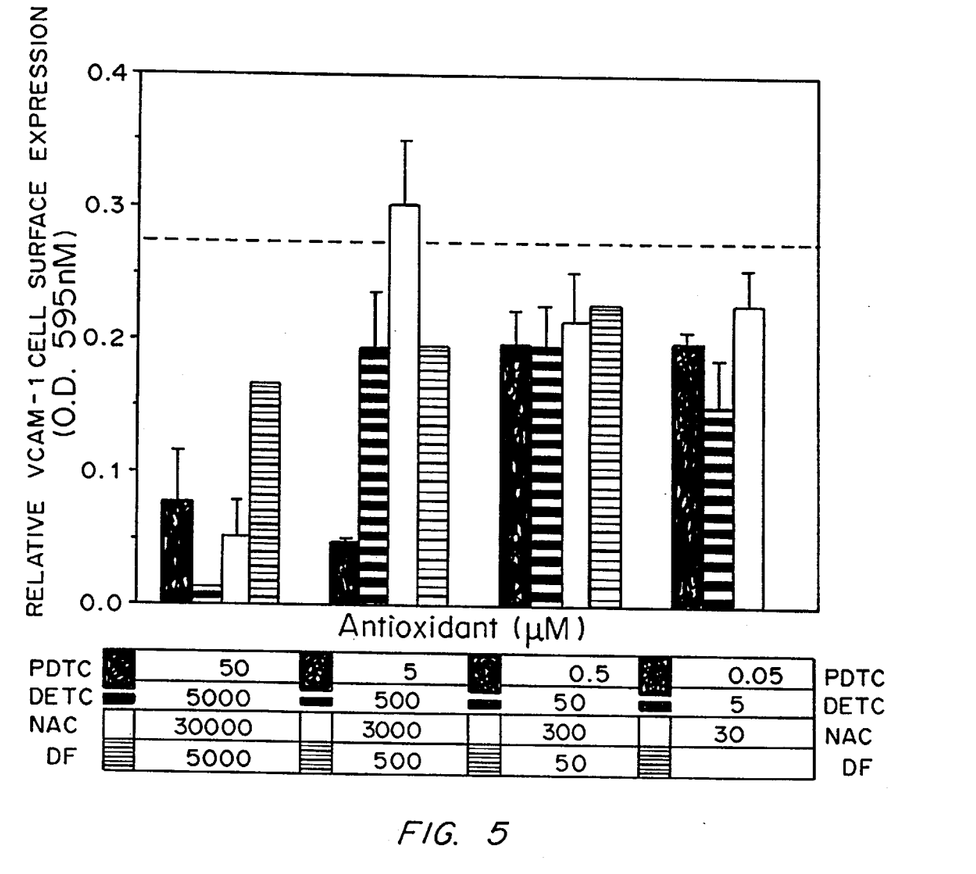
FIG. 5 is a graph of the relative VCAM-1 cell surface expression (O.D. 595 nM) in human umbilical vein endothelial cells, activated by TNFa, versus concentration of various antioxidants. (PDTC is sodium N-pyrrolidine dithiocarbamate; DETC is sodium N,N-diethyl-N-carbodithiolate, also referred to as sodium diethyldithiocarbamate; NAC is N-acetyl cysteine; and DF is desferroximine).

To determine whether structurally similar or dissimilar antioxidants could also inhibit VCAM-1 gene expression, and with what potency, HUVE cells were exposed to TNFa for six hours in the presence or absence of different concentrations of four different antioxidants. As shown in FIG. 5, both diethyldithiocarbamate (DETC) and N-acetyl cysteine (NAC) inhibited VCAM-1 expression at concentrations of 5 µM and 30 µM, respectively. In contrast, PDTC (PDTC) was effective between 5 and 50 µM. The iron metal chelator, desferroximine, had no effect at the concentrations tested.

EXAMPLE 5

PDTC Inhibits TNF Induction of VCAM-1/VLA-4 Mediated Adhesion

Figure 6:
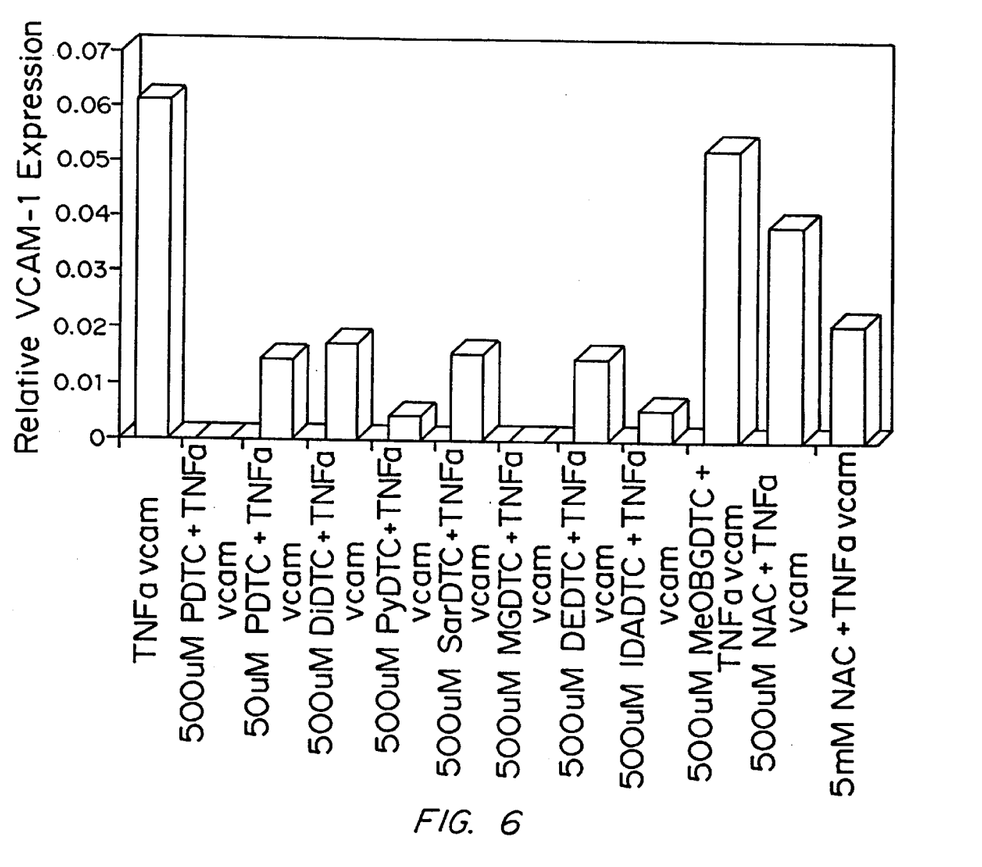
FIG. 6 is a graph of the relative VCAM-1 cell surface expression (O.D. 595 nM) in human umbilical vein endothelial cells, activated by TNFa, in the presence of the specified amount of antioxidant. (PDTC is sodium N-pyrrolidine dithiocarbamate; DIDTC is sodium N,N-diethyl-N-carbodithioate; SarDTC is sodium N-methyl-N-carbodithioate; IDADTC is trisodium N,N-di(carboxymethyl)-N-carbodithioate; MGDTC is sodium N-methyl-D-glucamine-N-carbodithioate; MeOB-GDTC is sodium N-(4-methoxybenzyl)-D-glucamine-N-carbodithioate; DEDTC is sodium N,N-diethyl-N-carbodithioate; Di-PDTC is sodium N,N-diisopropyl-N-carbodithioate; NAC is N-acetyl cysteine.)
Figure 7A:
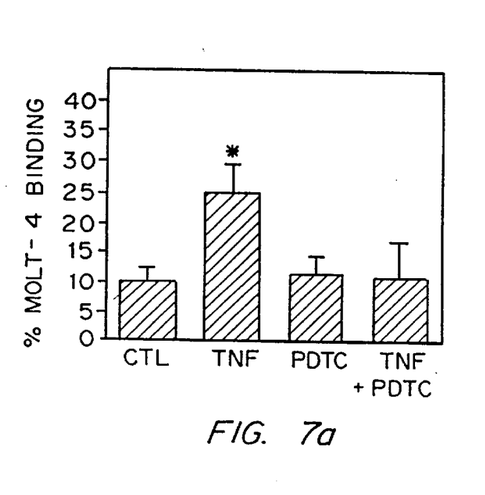
FIGS. 7A and 7B are graphs of the percentage of Molt-4 cells binding to HUVE cells either unstimulated or stimulated with TNFa (100 U/ml) for six hours in the presence or absence of PDTC.
Figure 7B:
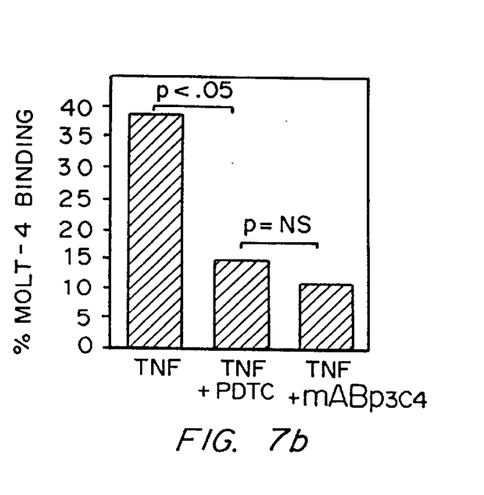

The ability of a variety of antioxidants to inhibit TNFa induction of VCAM-1 in HUVE cells was evaluated by the method set out in Example 4. FIG. 6 is a graph of the relative VCAM-1 cell surface expression (O.D. 595 nM) in TNFa activated HUVE cells versus concentrations of PTDC (sodium N-pyrrolidine dithiocarbamate), DIDTC (sodium N,N-diethyl-N-carbodithioate), SarDTC (sodium N-methyl-N-carboxymethyl-N-carbodithioate), IDADTC (trisodium N,N-di(carboxymethyl)-N-carbodithioate), MGDTC (sodium N-methyl-D-glucamine-N-carbodithioate), MeOB-GDTC (sodium N-(4-methoxybenzyl)-D-glucamine-N-carbodithioate), DEDTC (sodium N,N-diethyl-N-carbodithioate), Di-PDTC (sodium N,N-diisopropyl-N-carbodithioate), and NAC is (N-acetyl cysteine). The least effective compounds were MeOBGDTC and NAC.

EXAMPLE 6

PDTC Inhibits TNF Induction of VCAM-1/VLA-4 Mediated Adhesion

In order to define whether PDTC inhibition of VCAM-1 regulation is associated with functional consequences, the binding of Molt-4 cells to HUVEC cells either unstimulated or stimulated with TNF-a (100 U/ml) for six hours in the presence or absence of PDTC was examined. Molt-4 cells have been previously shown to bind to activated HUVEC via a VCAM-1 dependent mechanism. As shown in FIG. 6, the percentage of Molt-4 binding to HUVEC cells decreased when PDTC was present in the media.

EXAMPLE 7

PDTC Inhibits Monocyte Binding to the Thoracic Aorta of Cholesterol Fed Rabbits An experiment was performed to determine whether the thiol antioxidant PDTC would be efficacious in blocking the first monocyte binding component of atherosclerosis in an experimental animal model. One mature New Zealand white rabbit (3.5 Kg) received an intravenous injection of PDTC (20 mg/Kg, as a concentration of 20 mg/ml in PBS) once daily for 5 days. Injections were given via an indwelling cannula in the marginal ear vein, which was kept patent by flushing with heparinized saline solution. The PDTC solution was mixed fresh daily or on alternate days (stored light-protected at 4° C.), and filtered (0.45 mm pore filter) just prior to use. After the first injection, when the cannula was placed, the drug was administered with the rabbit in the conscious state without apparent discomfort or other ill effect. On the second day of injections, the rabbit was given chow containing 1% cholesterol by weight, which was continued throughout the remainder of the experiment. On the fifth day, the animal was euthanized and the thoracic aorta was excised and fixed. After appropriate preparation, the sample was imaged on the lower stage of an ISI DS-130 scanning electron microscope equipped with a LaB emitter. Using dual-screen imaging and a transparent grid on the CRT screen, 64 adjacent fields at a 620x magnification were assessed, to cover an area of approximately 1.3 $mm^2$. Within each field, the number of adherent leukocytes (WBC) and erythrocytes (RBC) were counted and recorded.

The data from the arch sample are as follows: 5 WBC and ~25 RBC per 1.3 $mm^2$ field. This level of WBC adhesion is similar to control animals fed regular chow (about 7 per field have been seen in arch and thoracic samples from 2 'negative control' experiments). 'Positive control' rabbits fed 1% cholesterol for 4 days but not given antioxidant show about a 5-fold increase in adhesion, to 38 WBC/1.3 $mm^2$. A considerable amount of mostly cell-sized debris was observed adherent to each arch sample. It is unclear whether this material is an artifact of preparation, or was present in vivo, and if so, whether it is related to PDTC administration. These studies suggest that PDTC infusions can effectively block initial monocyte adhesion to the aortic endothelium.

III. Pharmaceutical Compositions

Humans, and other animals, in particular, mammals, suffering from cardiovascular disorders, and other inflammatory conditions mediated by VCAM-1 can be treated by administering to the patient an effective amount of one or more of the above-identified compounds or a pharmaceutically acceptable derivative or salt thereof in a pharmaceutically acceptable carrier or diluent. The active materials can be administered by any appropriate route, for example, orally, parenterally, intravenously, intradermally, or subcutaneously.

As used herein, the term pharmaceutically acceptable salts or complexes refers to salts or complexes that retain the desired biological activity of the above-identified compounds and exhibit minimal undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid; (b) base addition salts formed with polyvalent metal cations such as zinc, calcium, bismuth, barium, magnesium, aluminum, copper, cobalt, nickel, cadmium, sodium, potassium, and the like, or with an organic cation formed from N,N-dibenzylethylene-diamine, D-glucosamine, ammonium, tetraethylammonium, or ethylenediamine; or (c) combinations of (a) and (b); e.g., a zinc tannate salt or the like.

The active compound is included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 0.5 to 500 mg/kg, preferably 1 to 100 mg/kg per day. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The compound is conveniently administered in any suitable unit dosage form, including but not limited to one containing 1 to 3000 mg, preferably 5 to 500 mg of active ingredient per unit dosage form. A oral dosage of 25–250 mg is usually convenient.

The active ingredient should be administered to achieve peak plasma concentrations of the active compound of about 0.1 to 100 $\mu M$, preferably about 1–10 $\mu M$. This may be achieved, for example, by the intravenous injection of a solution or formulation of the active ingredient, optionally in saline, or an aqueous medium or administered as a bolus of the active ingredient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable derivatives or salts thereof can also be administered with other active materials that do not impair the desired action, or with materials that supplement the desired action, such as antibiotics, antifungals, antiinflammatories, or antiviral compounds. The active compounds can be administered with lipid lowering agents such as probucol and nicotinic acid; platelet aggregation inhibitors such as aspirin; antithrombotic agents such as coumadin; calcium channel blockers such as varapamil, diltiazem, and nifedipine; angiotensin converting enzyme (ACE) inhibitors such as captopril and enalopril, and β-blockers such as propanalol, terbutalol, and labetalol. The compounds can also be administered in combination with nonsteroidal antiinflammatories such as ibuprofen, indomethacin, aspirin, fenoprofen, mefenamic acid, flufenamic acid, sulindac. The compound can also be administered with corticosteriods.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

The active compound can also be administered through a transdermal patch. Methods for preparing transdermal patches are known to those skilled in the art. For example, see Brown, L., and Langer, R., Transdermal Delivery of Drugs, Annual Review of Medicine, 39:221–229 (1988), incorporated herein by reference.

In another embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

Modifications and variations of the present invention will be obvious to those skilled in the art from the foregoing detailed description of the invention. Such modifications and variations are intended to come within the scope of the appended claims.

We claim:

1. A method for treating inflammatory diseases by VCAM-1 expression in human cells comprising administering an effective amount of a dithiocarbamate of the formula:

wherein $R^1$ is H, sodium, potassium, or $NR^4R^5R^6R^7$, wherein $R^4$, $R^5$, $R^6$, and $R^7$ are independently hydrogen, $C_{1-6}$ linear, branched, or cyclic alkyl, hydroxy($C_{1-6}$)alkyl, or aryl, and $R^2$ and $R^3$ are independently $C_{1-10}$ linear, branched or cyclic alkyl; —(CHOH)$_n$(CH$_2$)$_n$OH, wherein n is independently 0–6; —(CH$_2$)$_n$CO$_2$R$^1$, —(CH$_2$)$_n$CO$_2$R$^8$; hydroxy($C_{1-6}$)alkyl—, or $R^2$ and $R^3$ together constitute a bridge of the formula —(CH$_2$)$_m$—, wherein m is 3–6, and wherein $R_8$ is alkyl, aryl, alkylaryl, or aralkyl or its pharmaceutically acceptable salt.

2. The method of claim 1, wherein the dithiocarbamate is selected from the group consisting of sodium pyrrolidine-N-carbodithioate, sodium N-methyl-N-carboxymethyl-N-carbodithioate, trisodium N,N-di(carboxymethyl)-N-carbodithioate, sodium N-methyl-D-glucamine-N-carbodithioate, sodium N,N-diethyl-N-carbodithioate (sodium diethyldithiocarbamate), and sodium N,N-diisopropyl-N-carbodithioate.

3. The method of claim 1, wherein the dithiocarbamate is sodium pyrrolidine-N-carbodithioate.

4. The method of claim 1, wherein $R^2$ is a $C_{1-10}$ linear, branched or cyclic alkyl group.

5. The method of claim 1, wherein $R^2$ is —(CHOH)$_n$(CH$_2$)$_n$OH, wherein n is independently 0–6.

6. The method of claim 1, wherein $R^2$ is selected from the group consisting of —(CH$_2$)$_n$CO$_2$R$^1$, —(CH$_2$)$_n$CO$_2$R$^8$; and hydroxy($C_{1-6}$)alkyl—, and wherein $R^8$ is alkyl, aryl, alkylaryl, or aralkyl.

7. The method of claim 1, wherein $R^2$ and $R^3$ together constitute a bridge of the formula —(CH$_2$)$_m$—, wherein m is 4.

8. The method of claim 1, wherein the dithiocarbamate is administered in a dosage of between 0.5 and 500 mg/kg body weight.

9. The method of claim 1, wherein the dithiocarbamate is administered by perfusion balloon catheter.

10. The method of claim 1 wherein the dithiocarbamate is in the form of a pharmaceutically acceptable salt.

11. The method of claim 1, wherein $R^8$ is methyl, propyl or butyl.

12. The method of claim 1, wherein m is 3–6.

13. The method of claim 1, wherein the dithiocarbamate is administered intravenously.

14. The method of claim 1, wherein the dithiocarbamate is administered orally.

* * * * *